United States Patent [19]

Polaschegg et al.

[11] Patent Number: 5,695,717
[45] Date of Patent: Dec. 9, 1997

[54] GAS EXCHANGE APPARATUS

[75] Inventors: Hans-Dietrich Polaschegg, Oberursel; Hans-Helmut Lewinsky, Frankfurt; Bernd Steinbach, Bad Homburg, all of Germany

[73] Assignee: Fresenius AG, Germany

[21] Appl. No.: 751,040

[22] Filed: Nov. 15, 1996

Related U.S. Application Data

[63] Continuation of Ser. No. 257,604, Jun. 9, 1994, abandoned.

[30] Foreign Application Priority Data

Jun. 18, 1993 [DE] Germany ............... 43 20 198.9

[51] Int. Cl.$^6$ ............... A61M 1/14; A61M 1/34
[52] U.S. Cl. ............... 422/48; 422/44; 604/4; 604/122; 604/126; 604/246; 210/500.3; 210/500.43
[58] Field of Search ............... 422/44, 48, 112; 604/4, 151, 122, 126, 246; 210/321.77, 645, 650, 651, 653, 85, 87, 90, 97, 500.43, 500.3

[56] References Cited

U.S. PATENT DOCUMENTS

| | | | |
|---|---|---|---|
| 4,402,940 | 9/1983 | Nose et al. | 424/101 |
| 4,828,543 | 5/1989 | Weiss et al. | 604/4 |
| 4,906,375 | 3/1990 | Heilmann | 210/500.23 |
| 4,923,598 | 5/1990 | Schal | 210/87 |
| 5,131,928 | 7/1992 | Blachman et al. | 55/16 |
| 5,211,850 | 5/1993 | Shettigar et al. | 210/645 |
| 5,244,930 | 9/1993 | Trudell | 521/99 |
| 5,294,401 | 3/1994 | Hagiwara | 422/48 |
| 5,358,482 | 10/1994 | Panzani | 604/6 |
| 5,366,630 | 11/1994 | Chevallet | 210/645 |

FOREIGN PATENT DOCUMENTS

| | | |
|---|---|---|
| 0 323 341 | 12/1988 | European Pat. Off. . |
| 3129064 A1 | 7/1981 | Germany . |
| 4028311 C1 | 6/1990 | Germany . |
| WO 93.11807 | 12/1991 | WIPO . |

*Primary Examiner*—Nina Bhat
*Attorney, Agent, or Firm*—Luderschmidt & Partner

[57] ABSTRACT

A gas exchange device (100) with an extracorporeal blood circuit (102) in which a blood pump (110) is connected, with a $CO_2$ exchange unit (112), and an oxygenator (128), whereby the gas exchange unit (112, 128) is in each case divided by a hydrophilic, water-wet membrane (114, 130) into a blood chamber (116, 132) and a gassing chamber (118, 134) which is under positive transmembrane pressure.

10 Claims, 3 Drawing Sheets

GAS EXCHANGE APPARATUS

This application is a continuation, of application No. 08/257,604 filed Jun. 9, 1994, now abandoned.

BACKGROUND OF THE INVENTION

The invention concerns a device for gas exchange, in particular oxygenation of blood, with a gas exchanger which is divided by a semipermeable membrane into a blood chamber and a gas exchange chamber, whereby an extracorporeal blood path is run through the blood chamber and a gas path is run through the gas exchange chamber.

In the gas exchange between a livid phase and a gaseous phase by means of microporous membranes, hydrophobic membranes are usually used. This is the case, for example, in extracorporeal membrane oxygenation (ECMO), during which blood is supplied with oxygen in the extracorporeal circuit, for example, during performance of an open-heart operation.

ECMO devices are described, for example, in ASAIO, Vol. XXXIV (1988), pp. 978–985. Likewise, a hydrophobic oxygenator is described in DE-A-31 29 064, which proposes the use of hydrophobic membrane materials, for example, in the form of hollow fibers, for oxygenation. There, in the extracorporeal circuit, blood is passed by on one side of a hydrophobic membrane, while oxygen is supplied in countercurrent on the other side of the membrane, such that a $CO_2/O_2$ exchange can take place via the pores of the membrane.

Two types of hydrophobic membranes are usually used, namely membranes consisting of a material which is hydrophobic per se, for example, polypropylene (PP), and membranes whose surface has been made hydrophobic by means of a hydrophobic material, for example, silicon.

Hydrophobic membranes made of hydrophobic materials, such as PP, have comparatively large pores of several 100 to 1000 nm and are available in the form of more than 1000 hollow fibers, which results in an active surface of as much as 6 $m^2$. Here, the blood flows either inside the hollow fibers or even on the outside of the hollow fiber, while the gas to be exchanged flows by on the opposite side in countercurrent. These membranes are usually used in heart-lung machines.

On the other hand, membranes which have been made hydrophobic comprise a thin layer of silicon on a porous substrate and are—as explained in the following—used for long-term ECMO treatment.

It is true that hydrophobic membranes are more effective compared to siliconized membranes in terms of diffusion of the gases in the gas-filled pores, since the diffusion in pores is significantly faster than through liquid interfaces.

However, on the other hand, membranes made of porous hydrophobic material have a significant disadvantage in long-term therapy, i.e., therapy which extends over a period of more than 6 hours. This disadvantage involves leaks of the membrane, since despite their hydrophobic structure, the pores fill with aqueous plasma components, which results in a hydrophilization or wetting of the surface of the membrane. Since the hydrophobic membranes are used with a positive transmembrane pressure (TMP) considered from the blood side to the gas side, the hydrophilization leads, on the one hand, to the free flow of the plasma from the blood side to the gas side, such that plasma can leave the oxygenator in liquid form or as foam, and, on the other hand, to an inhibition of gas diffusion by clogging the membranes with plasma, such that the efficiency of the device is drastically reduced. In such a case, the oxygenator must be replaced.

Siliconized membranes are on the other hand less efficient, but prevent a break-through of plasma and are thus used in long-term ECMO. Similarly, hydrophobic membranes have been used in the extracorporeal removal of $CO_2$ ($ECCO_2R$) from blood. Such a device is presented, for example, in DE-A-40 28 311.

It has already been proposed to use hydrophilic membranes for ECMO, for example, in IEEE 13 (1991), pp. 1557–1559. In the arrangement proposed therein, the oxygenation occurs in a plurality of circuits, which are respectively separated from each other by semipermeable membranes. Direct oxygenation occurs first with the usual hydrophobic oxygenator, along one side of which oxygen runs and whose other side is supplied with aqueous liquid. This aqueous liquid picks up oxygen in a specific partial pressure and releases it along a hydrophilic membrane to a blood circuit, i.e., an exchange of liquids with different gas contents occurs along the surface of the hydrophilic membrane. Such a device thus makes use of the classical hydrophobic membrane for the transfer of gaseous oxygen into an aqueous liquid.

It is an object of the invention to make available a device for gas exchange in blood which has high exchange output, on the one hand, and can also be used in long-term operation, on the other.

SUMMARY OF THE INVENTION

In accordance with the present invention, there is provided apparatus for gas exchange wherein the membrane is hydrophilic and is wet with water during operation and the gas path is supplied with oxygen-containing gas under positive transmembrane pressure from the gas side to the blood side during operation.

BRIEF DESCRIPTION OF THE DRAWINGS

The invention may be better understood with reference to the accompanying drawings, in which.

DETAILED DESCRIPTION OF THE INVENTION

Figure 1:
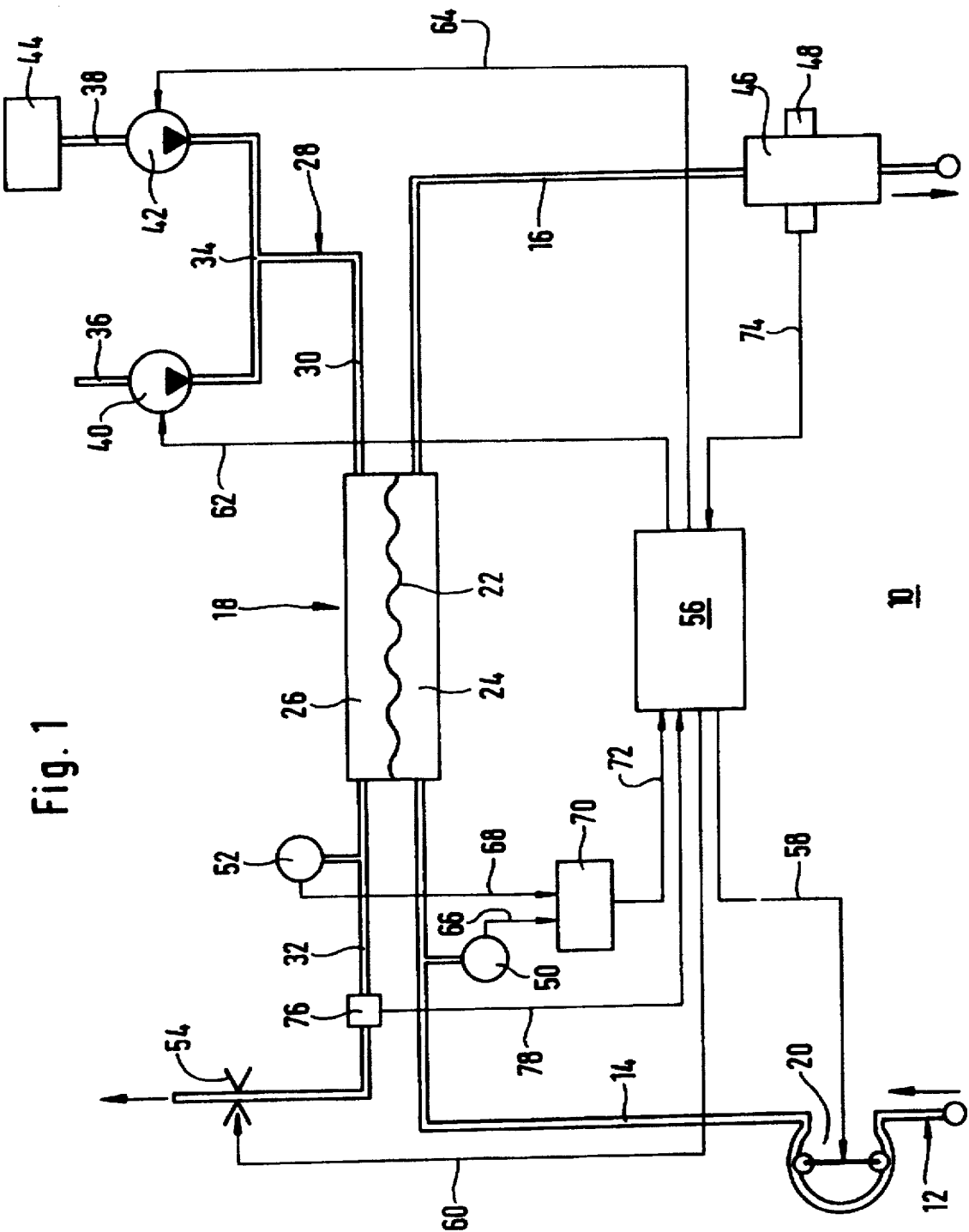
FIG. 1 schematically illustrates a first embodiment of a gas exchange device.

For purposes of the present invention, the term "hydrophilic membrane" is understood to mean all membranes wettable with water. First, this includes membranes which comprise one or a plurality of components containing hydrophilic material, such as regenerated cellulose or polysulfone, which is hydrophilized with polyvinylpyrrolidone (PVP) in specific amounts. A filter with the latter material is, for example, marketed by the applicant under the name PS 400 and is furthermore described in DE-A-34 26 331, to the entire contents of the publication of which reference is made. Additional suitable membrane materials are polyacrylonitrile, cellulose fibers (for example, as available under the trade designation Cuprophan from Akzo, Netherlands), cellulose acetate, and the like [see ed. Franz, Han Eduard, *Blutreinigungsverfahren*, Georg Thieme Verlag, Stuttgart, Germany (1990)]. It must be noted that these membranes have already been used for many years for hemodialysis and have proved themselves there.

As alternatives to membranes of already hydrophilic material, hydrophobic membranes can also be used if they have been made hydrophilic with hydrophilizing agents which can be washed out, such as myristyl alcohol or with a water/ethanol mixture. If, for example, the latter mixture is used, a membrane filled with this mixture can be wet directly by the introduction of water or of an aqueous electrolyte solution, i.e., all pores are then filled with the aqueous liquid. Another hydrophilizing method using sodium acetate is described, for example, in DE-A-30 43 073.

Finally, there is also the possibility of wetting hydrophobic membranes so that the lumen of hollow fibers is filled with an aqueous liquid and then subjected all around to pressure until the water has penetrated all pores.

It is also essential to the invention that the pores of the membrane are filled with aqueous liquid.

Preferably, according to the invention, membranes are used which already consist of hydrophilic material or of material made hydrophilic by hydrophilic additives. Hydrophilic membranes, as are described, for example, in DE-A-34 26 331, usually have an asymmetric form, i.e., they consist of a relatively thin skin of approximately 1 μm which is supported by a relatively coarse-pored support structure. The two structures are made of one and the same material, whereby the thin-pored membrane has pores with a relatively small diameter (between 2 and 20 nm). The gas exchange takes place through these pores via the column of liquid present in the pore, whereby the molecule in the gas stream is in equilibrium at the gas-liquid interface with the gas molecule physically dissolved in the liquid. Thus the liquid film found there acts as a barrier for gases similar to the silicon membrane with the difference that the exchange output is significantly greater, since the diffusion constant of dissolved oxygen in water is significantly higher compared to silicon.

The liquid found in a pore can be forced out of the pore as a function of the pore diameter and of the length of the pore at a specific pressure in that a gas is applied on the other side of the membrane with a specific overpressure. As soon as the pressure exceeds a specified value, the liquid is completely forced out of the pore, such that gas bubbles are visible in the liquid (so-called bubble-point pressure). This process is used to inspect hydrophilic membranes, for example, in hemodialyzers for detection of defects (large holes or broken capillaries). Usually, the bubble point of such membranes in water is at a value above 10 bar, such that membranes wet with water are leakproof up to 10 bar and can be supplied with gas without having to worry about penetration of the gas. But the partial pressure of gas in a liquid, which pressure is correlated with the amount of gas dissolved in the liquid, depends on the external pressure applied and/or the partial pressure of the respective gas components in the gas mixture (such as the oxygen component in air) with the consequence that the amount of gas to be delivered to the blood can be adjusted via the external pressure applied. Consequently, the oxygen concentration is adjusted by the selection of the air/oxygen mixture or of the pressure on this mixture.

As already mentioned, the membranes are advantageously present in the form of hollow fibers. However, on the other hand, flat membranes can also be used. The hollow fibers have an external diameter of 100 to 400 μm, advantageously approximately 200 μm, as well as an internal diameter of approximately 80 to 320 μm. The wall thickness is within a range from 10 to 60 μm.

Usually, a gas exchanging device according to the invention, in particular an oxygenator, includes up to 10,000 hollow fibers per unit, such that the entire membrane surface can be as much as 10 $m^2$.

In operation, the membrane wet with water serves as a liquid membrane through which the exchange or transfer of the gases takes place from the one medium gas to the other medium liquid. Consequently, free $CO_2$ found in the blood is exchanged at the membrane surface for the gas transferred from the other side of the membrane, which usually consists of air which has been enriched with oxygen in a predefined ratio. Advantageously, the gas is pressed against the liquid interface with a positive TMP (considered from the gas side to the blood side) into which it physically dissolves with the corresponding partial pressure. A transfer of gaseous components is excluded here because of the fact that the bubble point is not exceeded in the absolute overpressure selected. Thus, in contrast to hydrophobic membranes, with hydrophilic membranes wet with water, there is no risk that gas bubbles can be discharged directly into the bloodstream through the pores in the membrane and thus cause an air embolism. The latter can occur only if there is a rupture of the membrane surface such that air can enter the bloodstream. Thus, advantageously, safety devices in the form of air detectors are provided downstream from the gas exchange device, to reliably detect the formation of gas bubbles.

Such a release of air bubbles can also occur when supersaturation of the blood with oxygen-containing gas takes place because of too high a TMP compared to the ambient pressure, such that here again, advantageously, an air sensor is provided downstream from the gas exchange device. Such a supersaturation depends—as noted—on too high a TMP, which is adjusted relative to the two media, while the supersaturation occurs considered in absolute terms with regard to the ambient pressure.

According to a further aspect of the present invention, the exchange device is disposed upstream from a pump, in particular a blood pump, such that there is inevitably a partial vacuum in the suction region of the pump. If oxygenation is undertaken here, a specific oxygen/air concentration is set in the blood corresponding to the positive TMP, which blood can be supersaturated in the partial vacuum section. However, if the blood is transferred to the pressure side of the pump, the solubility of the gas in the blood is inevitably altered by the increase in pressure, i.e., more gas dissolves in the blood at the elevated pressure than with the lower suction pressure. Thus, a solution of the blood supersaturated with gas can be transferred by a pressure increase into a non-supersaturated region such that the formation of gas bubbles is effectively suppressed by such a device.

On the other hand, instead of the arrangement upstream from the blood pump, one embodiment can appear downstream from the blood pump, whereby the gas exchange device is disposed between a flow restricting device upstream and another pump downstream such that an artificial partial vacuum is produced by this.

According to a first embodiment, only one gas exchange device is provided in the extracorporeal circuit, which device is supplied on one side of the membrane with blood to be oxygenated and on the other side with a stream of gas with a predefined $O_2$ partial pressure (concentration), which can however be altered during the oxygenation. The stream of gas is supplied with a predefined or regulated overpressure in countercurrent to the membrane wet with water, such that $CO_2$ and the oxygen/air mixture are transferred reciprocally from one side of the membrane to the other.

In this embodiment, the delivery of the oxygen/air mixture can be either controlled or regulated. In the control case, the flow rate of the blood and the flow rate as well as the composition of the oxygen/air mixture including the transmembrane pressure are determined in advance, whereby predetermined pressure and flow values are maintained. If regulation occurs, an $O_2$ sensor, with which the actual $O_2$ concentration is measured, is provided downstream in the blood circuit from the gas exchanger. The value measured then serves as the actual value with which a comparison with a desired value is then performed, the result of which comparison can be used to change the composition or the overpressure of the gas mixture. According to the invention, the change in pressure can occur proportionally or intermittently at a pressure regulation valve or a gas restriction element. Whereas with the proportional pressure change the pressure is continually kept constant according to a specified value, with the intermittent operational mode there is a pulsed opening and closing of the valve, whereby the pressure is kept constant either by the relationship of the open times of the valve to the closed times or by the frequency of opening with constant open times. The regulation of the pressure requires a sensor in the gas area as well as an activation system for the regulating valve.

According to another embodiment, two gas exchangers are provided in the extracorporeal blood circuit, one of which is used for the $CO_2$ exchange, while the other exchanger connected downstream is used for pure oxygenation. Advantageously, the $CO_2$ exchanger is supplied with air, whereby a TMP of approximately 0 is used. The air is constantly supplied to the membrane and leaves the gas exchanger on the opposite side. Advantageously, the $CO_2$ partial pressure is determined downstream or upstream of the exchanger. The signal can be sent to a control unit which controls the flow of the air to set a specific $CO_2$ content downstream from the filter. The second gas exchanger is used for pure oxygenation and can have a smaller surface area than the first gas exchanger. Preferably, oxygen is supplied to the oxygenator in dead-end operation, i.e., this oxygenator has no gas outlet. The oxygen flow is set either by control or by regulation. In the regulated case, the oxygen partial pressure and/or the oxygen saturation is determined using a sensor downstream, and the signal is in turn sent to a regulating unit, which adjusts the oxygen flow accordingly. The oxygen partial pressure obtained or the supersaturation is set according to a value defined by the user (for example, an oxygen partial pressure of 0.25 bar or a supersaturation of 99%).

However, on the other hand it is also possible to operate the entire system under control in proportional operation, whereby the oxygen flow occurs in proportion to the blood flow. In such a case, the $CO_2/O_2$ exchange outputs of the two exchangers are brought into a relationship with the blood flow and thus are operated under control.

Compared to the conventional oxygenation system wherein hydrophobic oxygenators are used, the system according to the invention has significant advantages. It is possible to use standard or somewhat modified dialyzers which have membranes of comparatively biocompatible materials, such as polysulfone. The cost savings with this are significant, since dialyzers cost 10% less than membrane oxygenators. With the use of two exchangers, a gas mixer is no longer necessary, and the oxygen transfer can be adjusted independently of the $CO_2$ to be removed. This enables simple automatic control, which depends on only a single parameter, i.e., the oxygen or $CO_2$ content, which can be determined in each case with appropriate sensors. Oxygen consumption is limited to the oxygen needed by the patient. And finally, the $CO_2$ filter can also be used for removal of liquid without this having a significant negative effect on the $CO_2$ removal.

With the gas exchanger according to the invention, the sum of the partial pressures in the blood leaving the oxygenator should reach atmospheric pressure. This must not be significantly exceeded—as already explained—since otherwise there is the danger of air embolism.

FIG. 1 schematically depicts a gas exchange device 10. The gas exchange device has an extracorporeal blood circuit 12, which is divided into a feed line 14 and an discharge line 16 by a gas exchange unit 18. A blood pump 20 is connected in the feed line.

The gas exchange unit 18 is divided by a semipermeable membrane 22 into a blood chamber 24 and a gas exchange chamber 26. The extracorporeal blood circuit 12 is run through the blood chamber 24; the feed line 14 is connected to the input of the blood chamber 24 and the discharge line 16 is connected to its output, respectively.

A gas line 28, which is divided into a gas feed line 30 and a gas discharge line 32, is run through the gas exchange chamber. The end of the gas feed line 30 opens into a gas mixing point 34, to which an air feed line 36 and an oxygen feed line 38 are connected. Gas delivery elements 40 and 42 are connected respectively in the two feed lines 36 and 38. Whereas the air feed line 36 is connected to the ambient air, the oxygen feed line 38 is connected to an oxygen source 44. A drip chamber 46, which has a gas safety sensor 48, is connected in the discharge line 16.

The feed line 14 has, adjacent to the blood chamber 24, a first pressure sensor 50 to determine the pressure present in the blood. Likewise, a second pressure sensor 52, with which the gas pressure present in the gas line can be determined, is provided in the gas discharge line 32. And finally, a clamping arrangement 54, with which the cross-section of the gas feed line 32 can be altered, is provided at the end of the gas feed line 32.

The gas exchange device 10 is controlled by means of a control unit 56. For this the control unit 56 is linked via control lines 58–64 with the blood pump 20, the clamping arrangement 54, the first gas delivery element 40, and the second gas delivery element 42. The pressure sensors 50 and 52 send signals via signal lines 66 and 68 to a TMP measurement unit 70, whose signal is connected via signal line 72 with the control unit 56. Also, the control unit 56 is linked via a signal line 74 with the gas safety sensor 48. And finally, a $CO_2$ sensor 76, which is connected via a signal line 78 with the control unit 56, can be provided in the gas discharge line 32.

The gas exchange device is operated as follows. The extracorporeal circuit 12 is filled with a sterile physiological saline solution before connection to a patient, such that—as explained in the introduction—there is wetting of the hydrophilic membrane 22. Next, the extracorporeal circuit 12 is connected to the patient, and operation of the blood pump 20 is started at a predetermined speed by the control unit 56. A positive pressure is then set in the feed line 14 downstream from the blood pump 20 and upstream from the gas exchange unit 18, which is continuously determined by the pressure sensor 50 and fed to the TMP measurement unit 70. The control unit 56 further starts operation of the first gas delivery element 40 to feed air in a predefined manner and delivers this to the gas mixing point 34. Also, the second gas delivery element 42 is placed in operation in a predefined manner and delivers a predefined quantity of oxygen to the gas mixing point 34 at which an oxygen-air mixture with a predefined composition is mixed and delivered via the gas feed line 30 to the gas exchange chamber 26.

The gas pressure which is applied to the membrane 22 is adjusted by means of the controllable clamping arrangement 54 and measured by the pressure sensor 52, which likewise feeds its signal to the TMP measurement unit 70, in which the transmembrane pressure (TMP) is determined and sent to the control unit 56. According to a predefined program, which is stored in the control unit 56, oxygen is supplied at approximately 50 Nml/min, while simultaneously essentially the same amount of $CO_2$ is removed from the blood.

In this process, the $CO_2$ content can also be determined from the gas delivery rate of the gas delivery elements 40 and 42 and the $CO_2$ sensor 76 and adjusted for regulation purposes. With the gas exchange unit 10, a combined gas exchange of $CO_2$ and $O_2$ thus occurs according to the predefined partial pressures in the gas mixture or the TMP applied. This TMP is ultimately adjusted, on the one hand via the blood pump 20 and on the other via the clamping arrangement 54 as a function of the flow resistance of the gas exchanger 18 or the delivery rates of the gas delivery elements 40 and 42. At the output of the blood chamber, blood enriched in $CO_2$ and blood enriched in $O_2$ is obtained.

As already noted above, the device 10 depicted in FIG. 1 operates downstream from the blood pump 20 in the overpressure region, i.e., the blood is delivered at overpressure to the input of the blood chamber 24 and is usually delivered to the output of the blood chamber at ambient pressure. Since more gas dissolves in the blood at overpressure than at standard pressure, care must be taken according to the invention that no supersaturation of the blood occurs during oxygenation, which could lead to the formation of gas bubbles at the output of the blood chamber 24. Consequently, to prevent alarm situations, the TMP must be adjusted such that such overpressure conditions do not occur.

Figure 2:
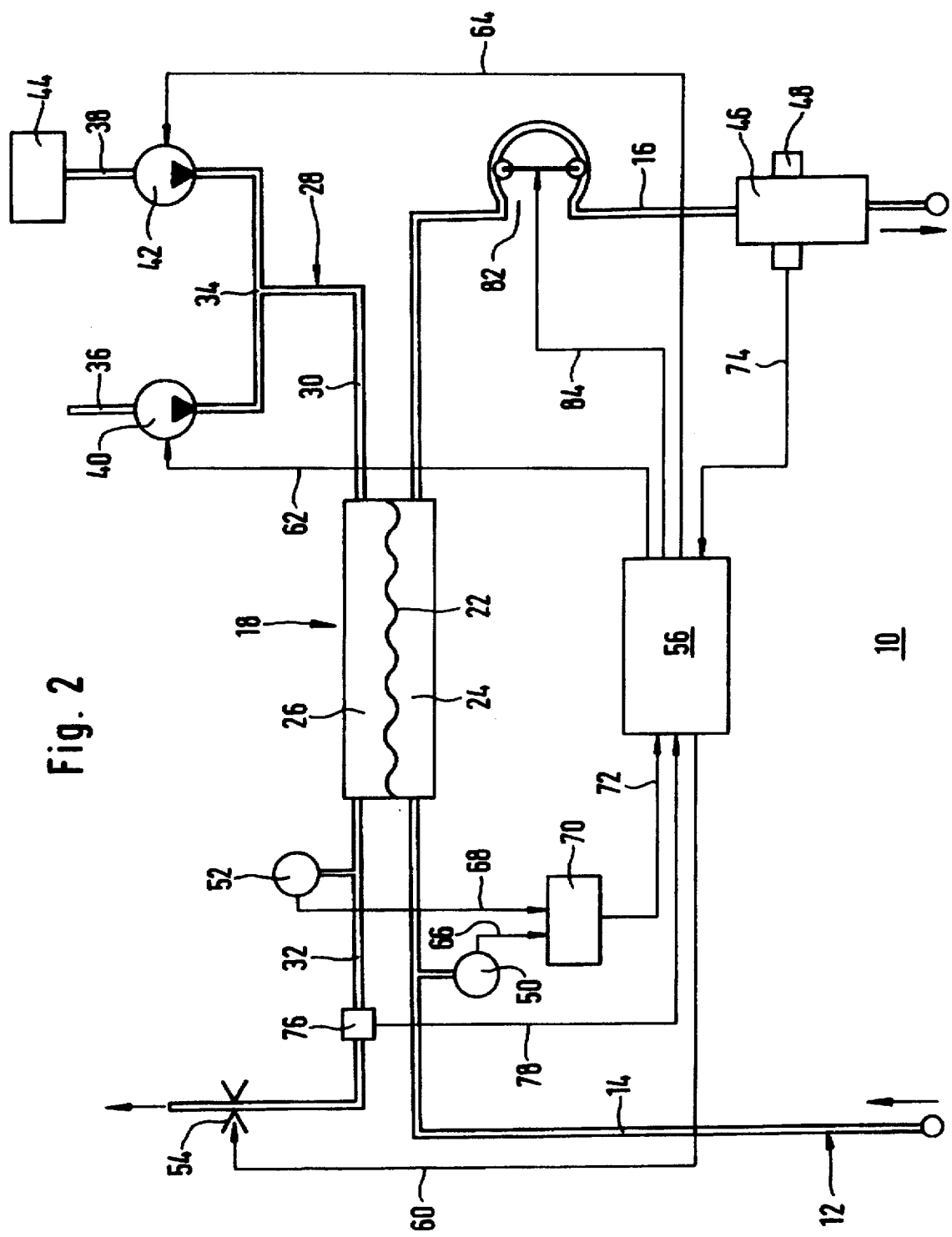
FIG. 2 schematically illustrates a second embodiment of a gas exchange device.

The embodiment depicted in FIG. 2 presents another gas exchange device 10, which is identical to the device 10 according to FIG. 1, except for the disposition of the blood pump 82, such that the same reference numbers are used as in FIG. 1.

The blood pump 82 is disposed downstream from the gas exchange device 18 in the feed line 16, but upstream from the pressure chamber 46 and is linked via a control line 84 with the control unit 56. Thus, the gas exchange unit 18 is located in the suction or partial vacuum zone of the blood pump 82 with the consequence that downstream from the blood pump 82 the gas-enriched blood is raised to ambient pressure such that inevitably the above described supersaturation problem is eliminated.

Figure 3:
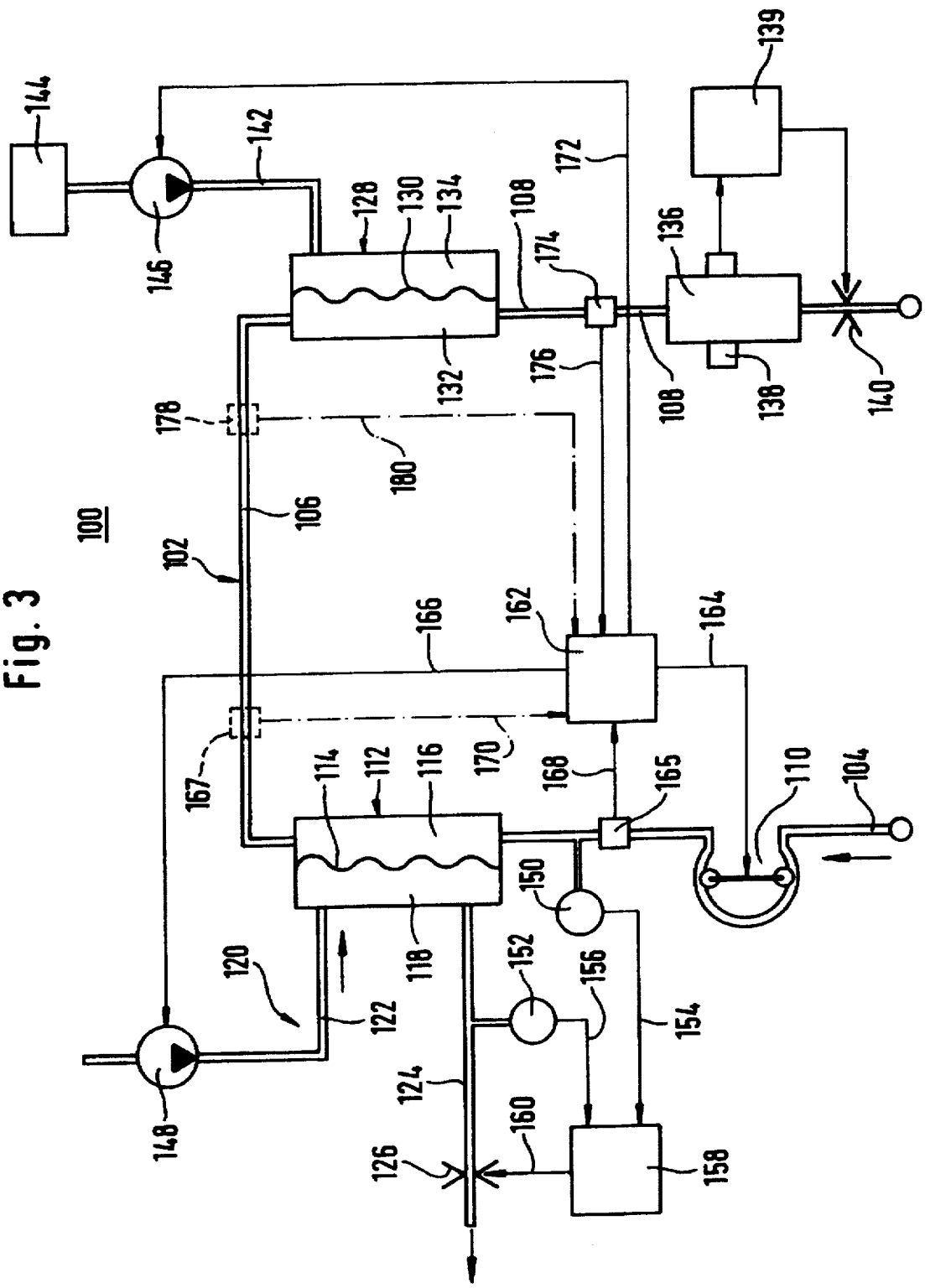
FIG. 3 schematically illustrates a third embodiment of a gas exchange device with a $CO_2$ exchanger and an oxygenator.

FIG. 3 depicts a third embodiment of a gas exchange device 100, which has an extracorporeal blood circuit 102, which is divided into a feed line 104, a transfer line 106, and a discharge line 108. A blood pump 110 is connected in the feed line 104. One end of the feed line 104 can be connected to a patient (not shown), while the other end is connected to a $CO_2$ exchanger, which has a semipermeable hydrophilized membrane 114, which divides the $CO_2$ exchanger into a blood chamber 116 and a degassing chamber 118. A degassing path 120, which is divided into a degassing feed line 112 and a degassing discharge line 124, is run through the degassing chamber 118.

At the output of the blood chamber 116, the transfer line 106 exits and is connected on its other end with an oxygenator 128, which is likewise divided by a hydrophilized semipermeable membrane 130 into a blood chamber 132 and an oxygenation chamber 134. The transfer line 106 opens into the blood chamber 132. The feed line 108, in which a drip chamber 136 equipped with a gas safety sensor 138 is connected, exits this blood chamber on the other side. Downstream from the drip chamber 136 a safety clamp 140 is provided on the feed line 108.

An oxygenation line 142, which advantageously has no discharge line and thus is operated in dead-end operation, opens into the oxygenation chamber 134. The oxygenation line 142 is linked with an oxygen source 144 and has an oxygen delivery element 146. A similar air delivery element 148, via which air is delivered, is provided at the input of the degassing line 120. These delivery elements can be designed as pumps or even as gas regulating valves or gas flow valves, if the gas to be delivered is already supplied with overpressure. Furthermore, a gas restriction element 126, with which the degassing pressure can be controlled in the degassing path 120, is provided at the output of the degassing line 124.

To determine the transmembrane pressure across the membrane 114, a first pressure sensor 150 is provided upstream from the $CO_2$ exchanger in the blood feed line 104, to determine the blood pressure in the feed line. A second pressure sensor 152 is provided in the degassing discharge line 124 downstream from the restrictor 126. Both pressure sensors 150 and 152 send their signal to a control unit 158 via control lines 154 and 156, which control unit determines the transmembrane pressure and compares the transmembrane pressure measured with a preset value and resets the gas restriction element 126 via the control line 160. However, on the other hand, the delivery rate of the blood pump 110 can also be appropriately adjusted.

Usually, the transmembrane pressure in the $CO_2$ exchanger 112 is set such that the two partial pressures rise such that the transmembrane pressure is roughly 0. If appropriate, an overpressure can be present on the blood side, if excess liquid is to be removed, which liquid is then removed through the gas removal line 124 serving as a filtrate line.

Furthermore, a main control unit 162, which controls the blood pump 110 via the control line 164 as well as the air delivery element 148 via a control line 166 according to a predefined $CO_2$ removal rate, is provided.

Advantageously, a $CO_2$ sensor can be provided either upstream or downstream from the $CO_2$ exchanger 112 in the feed line 104 or in the transfer line 106 as sensor 165 or 167, which are connected via signal lines 168 and 170, respectively, with the main control unit 162. By means of a signal from the $CO_2$ sensors 165, 167, it is possible with a known transmembrane pressure to adjust the stream of air to be delivered using the air delivery element 148 or the restrictor element 126.

The main control unit 162 is further connected via a control line 172 with the oxygen delivery element 146 and sets this to a predefined value.

Advantageously, an oxygen sensor 174, whose signal is connected with the main control unit 162 via the signal line 176, is provided downstream from the oxygenator 128 in the feed line 108. If the current oxygen content in the blood is determined with the oxygen sensor 174, this actual signal can be compared with a desired value in the main control unit 162, which then regulates the $O_2$ delivery element according to the results of the comparison performed. The air detector 138 is linked via a safety control 139, which closes the clamp 140 upon detection of air and switches the entire system into the safe state.

The device according to FIG. 3 is operated as follows. The entire extracorporeal circuit including the exchangers 112 and 128 is filled with physiological saline solution before connection to the patient, which—as explained in the introduction—results in the wetting of the hydrophilized membranes 114 and 130. These membranes then form an obstacle to the gases found in the chambers 118 and 134 impermeable up to the bubble-point pressure and also a liquid interface which can be used for diffusion of the gases to be exchanged.

After the filling of the device with the physiological saline solution, the patient is connected to the extracorporeal circuit 102 and the operation of the blood pump 110 is started at a predetermined speed. The delivery of air and oxygen then occurs in a predefined proportion or under regulation via the gas delivery elements 146 or 148. For this, the transmembrane pressure is measured by the pressure sensors 150 and 152 in the area of the $CO_2$ exchanger 112 and the gas restriction arrangement 126 is set such that the transmembrane pressure is roughly 0. The $CO_2$ exchanger itself can be set by the delivery rate of the gas delivery element 148, which can take place either empirically or from the determination of $CO_2$ upstream by means of the $CO_2$ sensor 164 or downstream by means of the $CO_2$ sensor 166 and an appropriate regulation through comparison of the actual value measured with a predefined desired value via the gas delivery element 148.

Likewise, the oxygenation in the oxygenator 118 is performed either empirically or with regulation. If control is executed, the oxygen overpressure to be set by means of the $O_2$ delivery element 146 is kept constant in a predefined manner such that the oxygenation of blood occurs via the membrane 130. However, on the other hand, the oxygen content in the blood can be determined downstream from the oxygenator 128 using the $O_2$ sensor 174. The actual value measured can then be compared with a preset desired value, such that the $O_2$ delivery element 146 can be regulated appropriately.

Advantageously, the oxygenator has a smaller membrane surface than the $CO_2$ degasser 112, which is usually approximately 1.8 $m^2$, whereas the oxygenator usually has a membrane surface of approximately 1 $m^2$. Oxygen partial pressures are approximately 0.25 bar, whereas the oxygen saturation amounts to as much as 99%. And finally, an additional oxygen sensor 178, which is connected via an additional signal line 180 with the main control unit 162, can be provided upstream from the oxygenator 128. This $O_2$ sensor can be used in addition to or even without the $O_2$ sensor 174 for control or regulation purposes.

What is claimed is:

1. A device for extracorporeal gas exchange with a body fluid comprising at least one gas exchanger including a semipermeable membrane which is hydrophilized and wetted with water so that the pores of the membrane are filled with an aqueous liquid, the membrane dividing the gas exchanger into a blood chamber and a gas exchange chamber, an extracorporeal blood path running through the blood chamber and a gas path running through the gas exchange chamber; a blood pump operatively connected in the blood path; and means for supplying oxygen-containing gas under positive transmembrane pressure in the gas path in the direction from the gas side to the blood side so that the amount of oxygen to be delivered to the blood can be controlled via the pressure of the gas in the gas path.

2. The device according to claim 1, wherein the blood pump is disposed upstream or downstream from the gas exchanger.

3. The device according to claim 1, wherein a first gas exchanger as a $CO_2$ exchanger and a second gas exchanger as an oxygenator are disposed consecutively in the extracorporeal blood path.

4. The device according to claim 3, wherein a degassing path which is provided on the feed side with a controllable air delivery element and on the air discharge side with a variable gas restrictor element is disposed in the degassing chamber of the first gas exchanger and the transmembrane pressure on the membrane of the first gas exchanger is adjustable with a transmembrane pressure control unit.

5. The device according to claim 3, wherein the second gas exchanger is linked with an oxygen source via an oxygenation line, in which a controllable oxygen delivery element is connected.

6. The device according to claim 3, wherein at least one $CO_2$ sensor, whose signal is connected as an actual value to a main control unit which compares the actual value with a desired value and regulates the gas flow of the first gas exchanger based on the result of the comparison, is provided in the extracorporeal blood path.

7. The device according to claim 3, wherein at least one $O_2$ sensor, whose signal is connected as an actual value to the main control unit which compares the actual value with a desired value and regulates the adjustable $O_2$ flow of the $O_2$ delivery element based on the result of the comparison, is provided in the extracorporeal blood circuit.

8. The device according to claim 1, wherein the membrane is made of a hydrophilic material.

9. The device according to claim 8, wherein the hydrophilic material is a mixture of polysulfone and polyvinylpyrrolidone.

10. The device according to claim 1, wherein the membrane is asymmetric and has a microporous skin layer and a coarse-pored support layer, whereby the average pore size in the skin layer is between 2 and 20 nm and the thickness of the skin layer is a maximum of several microns.

* * * * *